April 18, 1972 F. W. ANDERSON Plant Pat. 3,125
ALMOND TREE
Filed May 4, 1970
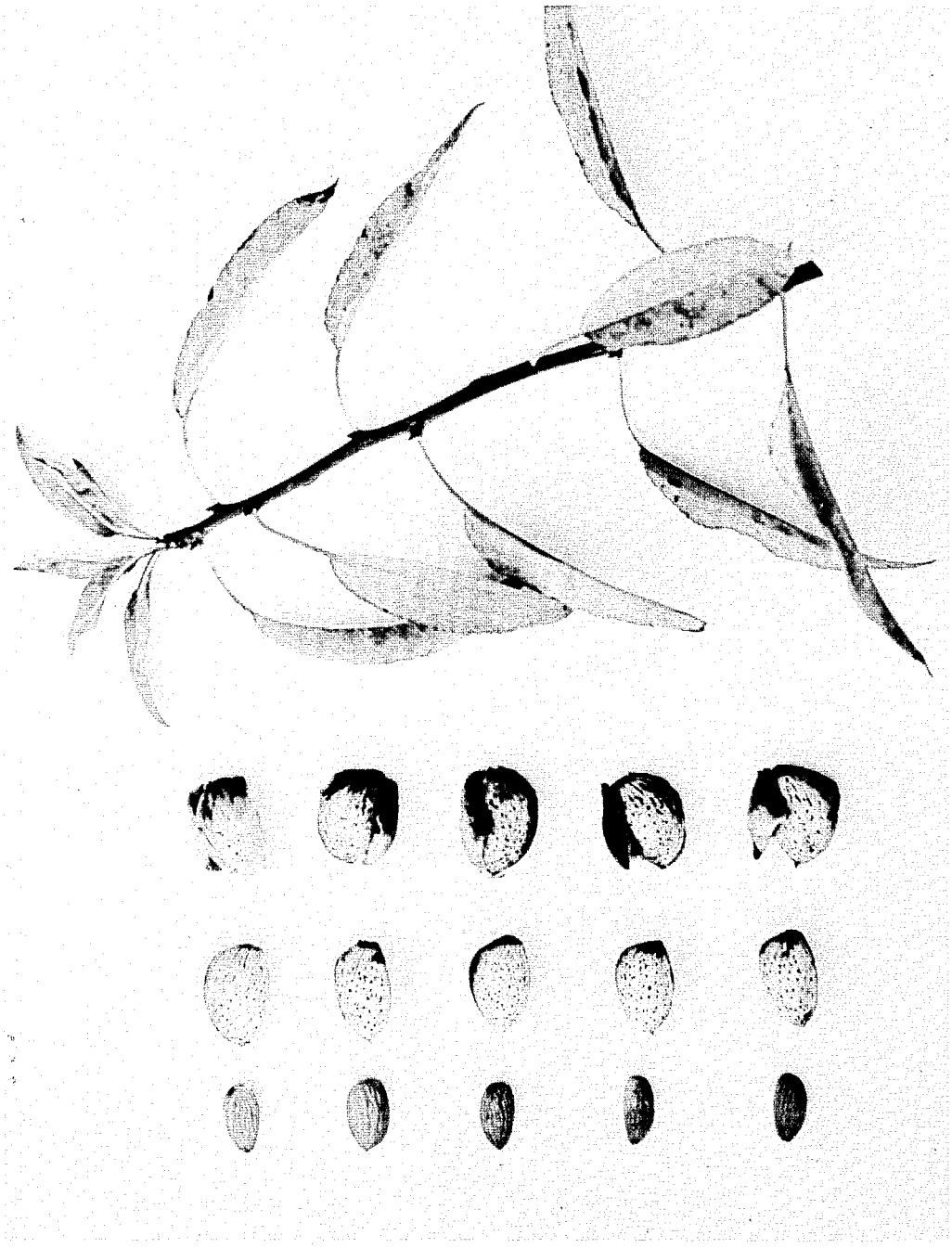
INVENTOR
Frederic W. Anderson
BY
Webster & Webster
ATTORNEYS United States Patent Office Plant Pat. 3,125
Patented Apr. 18, 1972

3,125

ALMOND TREE

Frederic W. Anderson, Merced, Calif., assignor to Arthur Bright, Le Grand, Calif.

Filed May 4, 1970, Ser. No. 34,643
Int. Cl. A01h 5/03
U.S. Cl. Plt.—30 1 Claim

ABSTRACT OF THE DISCLOSURE

A large, vigorous, open, medium to upright almond tree having abundant foliage with large to medium size ovate leaves, heavy white bloom, and well distributed, medium size, well sealed nuts borne regularly and heavily, and which nuts harvest early and approximately with the Nonpareil (unpatented).

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of nut trees. The present variety of almond tree resulted from my endeavors in the conduct of such plant breeding program.

ORIGIN OF THE VARIETY

The present variety of almond tree (which is a sib of the variety disclosed in United States Plant Patent No. 2,379) was originated by me in my experimental nursery, located as aforesaid, as an open-pollinated seedling of an unnamed almond variety closely resembling the Nonpareil but blooming about two weeks later.

Such open-pollinated seedling was maintained by me under careful and continuing observation, and—upon recognition of its novel and distinctive characteristics—I selected such variety for asexual reproduction preparatory to ultimate introduction to the trade.

ASEXUAL REPRODUCTION OF THE VARIETY

Subsequent to origination and selection by me of the present variety of almond tree, in the manner above described, I asexually reproduced it by grafting on mature trees in my said experimental orchard, and in maturity such reproductions ran true to the original tree in all respects.

SUMMARY OF THE VARIETY

The herein claimed variety of almond tree is of large size, vigorous, open, medium to upright in growth, abundant in foliage with large to medium size ovate leaves, blooms white and heavily, and is a regular and heavy bearer of well distributed, medium size, well sealed nuts which harvest early.

As compared to the Nonpareil, the herein claimed variety of almond tree is more vigorous, blooms approximately one week later, and produces nuts which harvest at approximately the same time; the shell being harder and better sealed, and hence the nuts are much less susceptible to damage by birds and insects, and contamination from organisms found in dust and soil. Eating quality of the nuts is better than the Nonpareil.

BRIEF DESCRIPTION OF THE DRAWING

The drawing is an illustration, by photographic reproduction in color, of a twig with leaves, nuts in hull, nuts out of hull, and separate kernels.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Open.
- *Size.*—Large.
- *Vigor.*—Vigorous.

Trunk:
- *Form.*—Medium.
- *Texture.*—Medium.

Branches:
- *Form.*—Medium.
- *Texture.*—Smooth.
- *Branching habit.*—Medium to upright.
- *Color.*—New wood—red; mature wood—brown.

Foliage: *Quantity.*—Abundant.

Leaves:
- *Size.*—Large to medium; average length—3"; average width—1".
- *Shape.*—Ovate.
- *Thickness.*—Medium.
- *Texture.*—Smooth.
- *Margin.*—Crenate.
- *Petiole.*—Medium length.
- *Glands.*—Number—1 to 3; alternate; medium size; usually positioned on petiole and base of blade.
- *Color.*—Top side—medium green (21-K-7); under side—slightly lighter green (21-K-6).

Bloom:
- *Amount of bloom.*—Heavy.
- *Color.*—White.
- *Blooming period.*—March 1st–17th, 1970; approximately 2 to 3 days after Mission (unpatented), and approximately 1 week after Nonpareil.

Crop:
- *Bearing.*—Regular bearer.
- *Productivity.*—Heavy.
- *Distribution of nuts on tree.*—Well distributed.
- *Harvest period.*—Early—approximately with Nonpareil.
- *Tenacity.*—Hangs on tree well; easy to harvest; easy to shell.

Hull:
- *Outer surface.*—Smooth.
- *Form.*—Regular.
- *Thickness.*—Thin.
- *Dehiscence.*—Opens freely.
- *Splitting.*—Along suture.

Nut:
- *Size.* — Medium; average length — 1¼"; average width — ¾"; average thickness — ⅝"; average weight—approximately 14 to an ounce.
- *Form.* — Length/width — oval. Width/thickness — medium—flat.
- *Shell.*—Soft to hard; thin; smooth to ragged. Outer shell—hard. Inner shell—soft; well sealed.
- *Color.*—Medium light (Straw—11-F-5).
- *Base.*—Ventrally oblique.
- *Stem scar.*—Small.
- *Apex.*—Obtuse; blunt.
- *Wing.*—Broad.
- *Inner surface.*—Light color.
- *Ventral streak.*—Narrow; long; point acute.
- *Percentage of kernel to nut.*—Approximately 60%.

Kernel:

*Size.*—Medium; average length—1"; average width —½"; average thickness—5/16"; average weight—approximately 30 to an ounce.

*Form.* — Length/width — oval. Width/thickness—medium.

*Base.*—Square to ventrally oblique.

*Stem scar.*—Small.

*Apex.*—Obtuse.

*Texture.*—Smooth to slightly wrinkled.

*Pellicle.*—Thin.

*Pubescence.*—Smooth.

*Color.*—Medium light brown (13-I-8).

*Number of doubles.*—Few to medium.

*Defective kernels.*—Very few.

*Flavor.*—Sweet.

*Quality.*—Very good.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is of large size, vigorous, open, medium to upright in growth, abundant in foliage with large to medium size ovate leaves, white and heavy of bloom, and a regular and heavy bearer of well distributed, medium size, well sealed nuts; characterized, in comparison to the tree and nuts of the Nonpareil, by being more vigorous, blooming approximately one week later but harvesting at approximately the same time, and producing nuts of excellent quality which have a harder shell and are better sealed.

No references cited.

ROBERT E. BAGWILL, Primary Examiner